US012605387B2

(12) United States Patent
Paterson et al.

(10) Patent No.: US 12,605,387 B2
(45) Date of Patent: Apr. 21, 2026

(54) TREATMENT OF CANCERS USING PI3 KINASE ISOFORM MODULATORS

(71) Applicant: Secura Bio, Inc., Las Vegas, NV (US)

(72) Inventors: Daniel Paterson, Needham, MA (US); Jonathan A. Pachter, Wayland, MA (US); Hagop Youssoufian, Boston, MA (US); Stephanie Lustgarten, Needham, MA (US)

(73) Assignee: Secura Bio, Inc., Las Vegas, NV (US)

( * ) Notice: Subject to any disclaimer, the term of this patent is extended or adjusted under 35 U.S.C. 154(b) by 392 days.

(21) Appl. No.: 18/017,631

(22) PCT Filed: Jul. 24, 2020

(86) PCT No.: PCT/US2020/043488

§ 371 (c)(1),
(2) Date: Jan. 23, 2023

(87) PCT Pub. No.: WO2022/019920

PCT Pub. Date: Jan. 27, 2022

(65) Prior Publication Data

US 2023/0293534 A1 Sep. 21, 2023

(51) Int. Cl.
*A61K 31/52* (2006.01)
*A61P 35/00* (2006.01)

(52) U.S. Cl.
CPC .............. *A61K 31/52* (2013.01); *A61P 35/00* (2018.01)

(58) Field of Classification Search
CPC ........ A61K 31/52; A61K 31/152; A61P 35/00
See application file for complete search history.

(56) References Cited

U.S. PATENT DOCUMENTS

| | | | |
|---|---|---|---|
| 5,861,510 | A | 1/1999 | Piscopio et al. |
| 5,863,949 | A | 1/1999 | Robinson et al. |
| 7,030,242 | B2 | 4/2006 | Noe et al. |
| 7,230,004 | B2 | 6/2007 | Adams et al. |
| 7,812,164 | B2 | 10/2010 | Austad et al. |
| 2002/0006931 | A1 | 1/2002 | Beachy et al. |
| 2003/0113828 | A1 | 6/2003 | Ginsberg et al. |
| 2003/0158195 | A1 | 8/2003 | Cywin et al. |
| 2003/0229090 | A1 | 12/2003 | Cywin et al. |
| 2005/0075306 | A1 | 4/2005 | Schreiber et al. |
| 2005/0232969 | A1 | 10/2005 | Andre et al. |
| 2005/0267059 | A1 | 12/2005 | Beardsley et al. |
| 2006/0205731 | A1 | 9/2006 | Kodama et al. |
| 2006/0247262 | A1 | 11/2006 | Baenteli et al. |
| 2007/0021493 | A1 | 1/2007 | Guicherit et al. |
| 2007/0060546 | A1 | 3/2007 | Ruat et al. |
| 2007/0219152 | A1 | 9/2007 | Schreiber et al. |
| 2007/0219195 | A1 | 9/2007 | Goldstein et al. |
| 2008/0114024 | A1 | 5/2008 | Cywin et al. |
| 2008/0287420 | A1 | 11/2008 | Castro et al. |
| 2008/0293754 | A1 | 11/2008 | Austad et al. |
| 2008/0293755 | A1 | 11/2008 | Castro et al. |
| 2009/0012031 | A1 | 1/2009 | Chinnaiyan et al. |
| 2009/0171089 | A1 | 7/2009 | Cywin et al. |
| 2009/0203010 | A1 | 8/2009 | Beke et al. |
| 2009/0306214 | A1 | 12/2009 | Kaplan |
| 2009/0312310 | A1 | 12/2009 | Kawato et al. |
| 2009/0312319 | A1 | 12/2009 | Ren et al. |
| 2010/0002861 | A1 | 1/2010 | Gao et al. |
| 2010/0048567 | A1 | 2/2010 | Jia et al. |
| 2010/0093625 | A1 | 4/2010 | Tarasova et al. |
| 2010/0152159 | A1 | 6/2010 | Mitchell et al. |
| 2010/0152182 | A1 | 6/2010 | Baenteli et al. |
| 2010/0222420 | A1 | 9/2010 | Chinnaiyan et al. |
| 2010/0316649 | A1 | 12/2010 | Zhang et al. |
| 2011/0046165 | A1 | 2/2011 | Ren et al. |
| 2011/0053897 | A1 | 3/2011 | Che et al. |
| 2011/0112098 | A1 | 5/2011 | Dariavach et al. |
| 2011/0245205 | A1 | 10/2011 | Altman et al. |
| 2011/0251216 | A1 | 10/2011 | Chinnaiyan et al. |
| 2011/0275655 | A1 | 11/2011 | Atkinson et al. |
| 2011/0286990 | A1 | 11/2011 | Guo et al. |
| 2012/0014962 | A1 | 1/2012 | Mann et al. |
| 2012/0027834 | A1 | 2/2012 | Andre et al. |
| 2012/0071418 | A1 | 3/2012 | Copeland et al. |
| 2012/0093913 | A1 | 4/2012 | Schreiber et al. |
| 2012/0101275 | A1 | 4/2012 | Jia et al. |
| 2012/0130073 | A1 | 5/2012 | Jia et al. |
| 2012/0142671 | A1 | 6/2012 | Jia et al. |
| 2012/0184526 | A1 | 7/2012 | Che et al. |
| 2012/0184568 | A1 | 7/2012 | Ren et al. |
| 2012/0220582 | A1 | 8/2012 | Mitchell et al. |
| 2012/0277192 | A1 | 11/2012 | Altman et al. |

(Continued)

FOREIGN PATENT DOCUMENTS

| | | | |
|---|---|---|---|
| EP | 0606046 | A1 | 7/1994 |
| EP | 0780386 | A1 | 6/1997 |

(Continued)

OTHER PUBLICATIONS

Clinical Trial Identifier No. NCT04038359 (Record version Jul. 26, 2019). (Year: 2019).*

Berge, S.M. et al., "Pharmaceutical Salts," Journal of Pharmaceutical Sciences, Jan. 1977, vol. 66, No. 1, pp. 1-19.

Brown et al., "Idelalisib, an inhibilor of phosphatidylinositol 3-kinase p110delta, for relapsed/refractory chronic lympocytic leukemia," Blood 123(22): 3390-3397 (2014).

Buckley et al., "IRAK-4 inhibitors. Part 1 : a series of amides," Bioorganic & medicinal chemistry letters 2008, 18(11):3211-3214.

Buckley et al., "IRAK-4 inhibitors. Part II: A structure-based assessment of imidazo[1,2-a]pyridine binding," Bioorganic & medicinal chemistry letters 2008, 18(11):3291-3295.

(Continued)

*Primary Examiner* — Layla D Berry

(74) *Attorney, Agent, or Firm* — COOLEY LLP

(57) ABSTRACT

Provided herein, at least in part, are methods of treating a hematologic malignancy in a human subject in need thereof, comprising orally administering to the subject duvelisib or a pharmaceutically acceptable form thereof.

7 Claims, No Drawings

(56) References Cited

U.S. PATENT DOCUMENTS

| | | | |
|---|---|---|---|
| 2012/0309735 A1 | 12/2012 | Altman et al. |
| 2013/0040906 A1 | 2/2013 | Kuntz et al. |
| 2013/0040984 A1 | 2/2013 | Atkinson et al. |
| 2013/0090309 A1 | 4/2013 | Romeo et al. |
| 2013/0116260 A1 | 5/2013 | Arikawa et al. |
| 2013/0165431 A1 | 6/2013 | Jia et al. |
| 2013/0195843 A1 | 8/2013 | Morin et al. |
| 2014/0120083 A1 | 5/2014 | Stern et al. |
| 2019/0076425 A1 | 3/2019 | Srinivasan et al. |
| 2025/0032499 A1 | 1/2025 | Litwak et al. |

FOREIGN PATENT DOCUMENTS

| | | |
|---|---|---|
| EP | 0818442 A2 | 1/1998 |
| EP | 0931788 A2 | 7/1999 |
| EP | 0945864 A2 | 9/1999 |
| EP | 1004578 B1 | 2/2004 |
| WO | WO-9005719 A1 | 5/1990 |
| WO | WO-9627583 A1 | 9/1996 |
| WO | WO-9633172 A1 | 10/1996 |
| WO | WO-9803516 A1 | 1/1998 |
| WO | WO-9807697 A1 | 2/1998 |
| WO | WO-9830566 A1 | 7/1998 |
| WO | WO-9833768 A1 | 8/1998 |
| WO | WO-9834915 A1 | 8/1998 |
| WO | WO-9834918 A1 | 8/1998 |
| WO | WO-9907675 A1 | 2/1999 |
| WO | WO-9929667 A1 | 6/1999 |
| WO | WO-9952889 A1 | 10/1999 |
| WO | WO-9952910 A1 | 10/1999 |
| WO | WO-0119800 A2 | 3/2001 |
| WO | WO-0126644 A2 | 4/2001 |
| WO | WO-0127135 A2 | 4/2001 |
| WO | WO-0149279 A2 | 7/2001 |
| WO | WO-0174344 A2 | 10/2001 |
| WO | WO-03011219 A2 | 2/2003 |
| WO | WO-03030902 A1 | 4/2003 |
| WO | WO-03088970 A2 | 10/2003 |
| WO | WO-2004020599 A2 | 3/2004 |
| WO | WO-2004041285 A1 | 5/2004 |
| WO | WO-2005013800 A2 | 2/2005 |
| WO | WO-2005032343 A2 | 4/2005 |
| WO | WO-2005033288 A2 | 4/2005 |
| WO | WO-2005042700 A2 | 5/2005 |
| WO | WO-2005107758 A1 | 11/2005 |
| WO | WO-2005113556 A1 | 12/2005 |
| WO | WO-2006028958 A2 | 3/2006 |
| WO | WO-2006050351 A2 | 5/2006 |
| WO | WO-2006078283 A2 | 7/2006 |
| WO | WO-2007054623 A2 | 5/2007 |
| WO | WO-2007059157 A1 | 5/2007 |
| WO | WO-2007120827 A2 | 10/2007 |
| WO | WO-2007131201 A2 | 11/2007 |
| WO | WO-2008030579 A2 | 3/2008 |
| WO | WO-2008070357 A2 | 6/2008 |
| WO | WO-2008110611 A1 | 9/2008 |
| WO | WO-2008112913 A1 | 9/2008 |
| WO | WO-2008131354 A2 | 10/2008 |
| WO | WO-2009088086 A1 | 7/2009 |
| WO | WO-2009088990 A1 | 7/2009 |
| WO | WO-2009114870 A2 | 9/2009 |
| WO | WO-2010006086 A2 | 1/2010 |
| WO | WO-2010036380 A1 | 4/2010 |
| WO | WO-2011008302 A1 | 1/2011 |
| WO | WO-2014071109 A1 | 5/2014 |
| WO | WO-2014194254 A1 | 12/2014 |

OTHER PUBLICATIONS

Buckley et al., "IRAK-4 inhibitors. Part III: a series of imidazo[1,2-a]pyridines," Bioorganic & medicinal chemistry letters 2008, 18(11):3656-3660.

Bundegaard, H., "Design of prodrugs: Bioreversible derivatives for various functional groups and chemical entities", Design of Prodrugs, 1985, p. 1-92.

Cheson et al. "Novel Targeted Agents and the Need to Refine Clinical End Points in Chronic Lymphocytic Leukemia". Journal of Clinical Oncology, vol. 30, No. 23, pp. 2820-2822, Aug. 10, 2012.

Cheson et al., "Recommendations for Initial Evaluation, Staging, and Response Assessment of Hodgkin and Non-Hodgkin Lymphoma: The Lugano Classification," J Clin Oncol 2014;32(27):3059-3067.

Clayton et al., "A crucial role for the P110 delta subunit of phosphatidylinositol 3-kinase in B cell development and activation," J. Exp. Med. 196(6): 753-763 (2002).

Elbashir, et al. "Duplexes of 21-nucleotide RNAs mediate RNA interference in cultured mammalian cells." Nature (2001); 411(6836): 494-498.

Flinn et al. Duvelisib, an oral dual PI3K-delta, gamma inhibitor, shows clinical activity in indolent non-Hodgkin lymphoma in a phase 1 study. Am J Hematol. 1311-1317, (2018).

Fung-Leung, W. P., "Phosphoinositide 3-kinase delta (PI3Kdelta) in leukocyte signaling and function," Cell Signal. 23(4): 603-608 (2011).

Hallek et al., "Guidelines for the diagnosis and treatment of chronic lymphocytic leukemia: a report from the International Workshop on Chronic Lymphocytic Leukemia updating the National Cancer Institute—Working Group 1996 guidelines," Blood. Jun. 15, 2008;111(12):5446-5456.

Higuchi and Stella, "Pro-drugs as Novel Drug Delivery Systems," A.C.S. Symposium Series, vol. 14, Chp 1, pp. 1-6, Jun. 1, 1975.

International Search Report and Written Opinion Issued by the International Searching Authority for Application No. PCT/US2020/043488, dated Oct. 23, 2020, 9 pages.

Knight et al., "A Pharmacological Map of the PI3-K Family Defines a Role for p110alpha in Insulin Signaling," Cell 125 (4): 733-747 (2006).

Lucas et al., "Design of I-piperazinyl-4-arylphthalazines as potent Smoothened antagonists," Bioorg. Med. Chem. Lett. 20:3618-3622 (2010).

National Institute of Health Clinical Trial Identifier No. NCT00670189, dated Aug. 15, 2014, 13 pages.

National Institute of Health Clinical Trial Identifier No. NCT00953758 dated Aug. 6, 2009, 6 pages.

National Institute of Health Clinical Trial Identifier No. NCT01106508, dated Apr. 20, 2010, 6 pages.

Okkenhaug et al., "Impaired Band T Cell Antigen Receptor Signaling in pl 108 PI 3-Kinase Mutant Mice," Science 297:1031-1034 (2002).

Pan et al., "Discovery of NVP-LDE225, a Potent and Selective Smoothened Antagonist," ACS Med. Chem. Lett. 1:130-134 (2010).

Robarge et al., "GDC-0449—A potent inhibitor of the hedgehog pathway," Bioorg. Med. Chem. Lett. 19:5576-5581 (2009).

Rominger et al., "Evidence for Allosteric Interactions of Antagonist Binding to the Smoothened Receptor," J. Pharmacol. Exp Ther. 329(3):995-1005 (2009).

Rudin et al., "Treatment of Medulloblastoma with Hedgehog Pathway Inhibitor GDC-0449," N. Engl. J. Med. 361(12):1173-1178 (2009).

Siu et al., "A first-in-human, phase I study of an oral hedgehog (HH) pathway antagonist, BMS-833923 (XL139), in subjects with advanced or metastatic solid tumors," J. Clin. Oncol. 28(15_suppl):2501, 2 pages. (ASCO Annual Meeting Abstracts 2010).

Vanhaesebroeck et al., "PI3K: From the Bench to the Clinic and Back," Curr. Top. Microbiol. Immunol. 347: 1-19 (2010).

Verastem, Inc. Experimental: IPI-145. Nov. 22, 2011, https://clinicaltrials.gov/ct2/show/NCT01476657, 6 pages.

Von Hoff et al., "Inhibition of the Hedgehog Pathway in Advanced Basal-Cell Carcinoma," N. Engl. J. Med. 361(12):1164-1672 (2009).

Yauch et al., "Smoothened Mutation Confers Resistance to a Hedgehog Pathway Inhibitor in Medulloblastoma," Science 326:572-574 (2009).

Extended European Search Report for EP Application No. 20200945788, dated Apr. 4, 2024, 18 pages.

Flinn et al., Duvelisib, a novel oral dual inhibitor of PI3K-δ, γ, is clinically active in advanced hematologic malignancies. Blood. 131(8):877-887. (Feb. 22, 2018). Epub Nov. 30, 2017.

(56) References Cited

OTHER PUBLICATIONS

Flinn et al., "DYNAMO: A Phase II Study of Duvelisib (IPI-145) in Patients With Refractory Indolent Non-Hodgkin Lymphoma," Journal of Clinical Oncology 37(11)912-922 (Apr. 10, 2019).
Horwitz et al. "Activity of the PI3K-[delta], [gamma] inhibitor duvelisib in a phase 1 trial and preclinical models of T-cell lymphoma," Blood 131(8):888-898 (Feb. 22, 2018).
Ito et al., Development of new agents for peripheral T-cell lymphoma, Expert Opinion On Biological Therapy 19(3):197-209 (Jan. 29, 2019).
Brammer, J. et al., "Duvelisib in Patients with Relapsed/Refractory Peripheral T-Cell Lymphoma from the Phase 2 Primo Trial: Results of an Interim Analysis," Blood, B63rd ASH Annual Meeting Abstracts, Poster Abstracts, vol. 138, Supplement 1, pp. 2456-2458 (Nov. 5, 2021).
Clinical Trial Identifier No. NCT03372057. SECURABIO, "A Study of Duvelisib in Participants With Relapsed or Refractory Peripheral T-cell Lymphoma (PTCL)," [ClinicalTrials.gov.] Version 25 (Mar. 5, 2025). [Retrieved from Internet on Nov. 11, 2025 at URL: https://clinicaltrials.gov/study/NCT03372057]; 58 pages.
Clinical Trial Identifier No. NCT03372057. SECURABIO, "A Study of Duvelisib in Participants With Relapsed or Refractory Peripheral T-cell Lymphoma (PTCL)," [ClinicalTrials.gov], Version 9 (Oct. 18, 2019). [Retrieved from Internet on Nov. 11, 2025 at URL: https://clinicaltrials.gov/study/NCT03372057]; 20 pages.
Clinical Trial Identifier No. NCT04038359. SECURABIO, "A Phase 2 Study Comparing 2 Intermittent Dosing Schedules of Duvelisib in Participants With Indolent Non-Hodgkin Lymphoma (TEMPO)," [ClinicalTrials.gov.], Version 22 (Sep. 4, 2024). [Retrieved from Internet on Nov. 11, 2025 at URL: https://clinicaltrials.gov/study/nct04038359]; 45 pages.
Jacobsen, E. et al., "Duvelisib in Patients with Relapsed/Refractory Peripheral T-Cell Lymphoma from the Phase 2 Primo Trial Expansion Phase: Impact of Prior Treatment and Expanded Safety Analysis," Blood, vol. 140, Supplement 1, 64th ASH Annual Meeting Abstracts, Poster Abstracts, pp. 9387-9389 (Nov. 15, 2022).
Mehta-Shah, N., Duvelisib in Patients With Relapsed/Refractory Peripheral T-cell Lymphoma: Final Results From the Phase 2 PRIMO Trial, Presented at ASH 2024, San Diego, CA Poster No. 3061, 4 total pages (Dec. 7-10, 2024).
Pro, B., et al., "Duvelisib in Patients with Relapsed/Refractory Peripheral T-Cell Lymphoma from the Phase 2 Primo Trial: Dose Optimization Efficacy Update and Expansion Phase Initial Results," Blood, vol. 136, Supplement 1, pp. 38-39, 6 pages total (Nov. 5, 2020).
Vorobyev, V.I. et al., "TEMPO: A Phase 2, Randomized, Open-Label, 2-Arm Study Comparing 2 Intermittent Dosing Schedules of Duvelisib in Subjects with Indolent Non Hodgkin Lymphoma (iNHL)," Blood, 63rd ASH Annual Meeting Abstracts, Poster Abstracts, vol. 138, Supplement 1, pp. 3545-3547 (Nov. 23, 2021).
Brammer, Jonathan E et al., "Duvelisib in Patients with Relapsed/Refractory Peripheral T-Cell Lymphoma from the Phase 2 Primo Trial: Results of an Interim Analysis," BLOOD, vol. 138, No. Supplement 1, pp. 2456-2456, 7 total p. (Nov. 5, 2021). - ASH Publications.
Database Accession No. EMB-625976788, Author: Horwitz, S.M et al., "The PRIMO study: A phase 2 study of duvelisib efficacy and safety in patients with relapsed or refractory peripheral t-cell lymphoma (Ptcl)", Journal of Clinical Oncology 20180501 American Society of Clinical Oncology Nld, vol. 36, No. 15, Supplement 1; [EMBASE] (Date: May 1, 2018), [Retrieved from https://www.embase.com/(RETRIEVAL Date Unknown]; 3 total pages.
EP Application No. 20945788.6, Office Action mailed Mar. 5, 2026; Applicant SECURA Bio, Inc .; 14 total pages.
Karmali R et al.; "A Phase 2, Randomized, Open-label, Arm Study Comparing 2 Intermittent Dosing Schedules of Duvelisib in Patients with Indolent Non-Hodgkin Lymphoma (iNHL) (TEMPO)", Blood, vol. 134 (Supplement_1), (Nov. 13, 2019), p. 5251.
Vorobyev V et al.; "P1123 Tempo: a Phase 2, Randomized, Open-label, Arm Study Comparing Two Intermittent Dosing Schedules of Duvelisib in Subjects with Indolent Non-hodgkin Lymphoma (INHL)", Topic: 18. Indolent and mantle-cell non-Hodgkin lymphoma -Clinical, (Jun. 1, 2022), pp. 1-2.
Zinzani P. L et al.; "P1172 Duvelisib in Patients with Relapsed/refractory Peripheral T-cell Lymphoma from the Phase 2 Primo Trial: Updated Expansion Phase Analysis", Topic: Topic: 19. Aggressive Non-Hodgkin lymphoma -Clinical, (Jun. 1, 2022), pp. 1-2.

* cited by examiner

TREATMENT OF CANCERS USING PI3 KINASE ISOFORM MODULATORS

CROSS-REFERENCE TO RELATED APPLICATIONS

This application is a U.S. National Phase application, filed under 35 U.S.C. § 371 (c), of International Application No. PCT/US2020/043488, filed Jul. 24, 2020, the contents of which are incorporated by reference in its entirety.

BACKGROUND

The phosphoinositide 3-kinases (PI3Ks) signaling pathway is one of the most highly mutated systems in human cancers. PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p10δ, and p110γ) are typically activated by tyrosine kinases or G-protein coupled receptors to generate phosphatidylinositol (3,4,5)-trisphosphate (PIP3), which engages downstream effectors such as those in the AKT/PDK1 pathway, mTOR, the Tec family kinases, and the Rho family GTPases. The class II and III PI3Ks play a key role in intracellular trafficking through the synthesis of phosphatidylinositol 3-bisphosphate (PI(3)P) and phosphatidylinositol (3,4)-bisphosphate (PI(3,4)P2). The PI3Ks are protein kinases that control cell growth (mTORC1) or monitor genomic integrity (ATM, ATR, DNA-PK, and hSmg-1).

There are four mammalian isoforms of class I PI3Ks: PI3K-α, β, δ (class Ia PI3Ks) and PI3K-γ (a class lb PI3K). These enzymes catalyze the production of PIP3, leading to activation of downstream effector pathways important for cellular survival, differentiation, and function. PI3K-α and PI3K-β are widely expressed and are important mediators of signaling from cell surface receptors. PI3K-α is the isoform most often found mutated in cancers and has a role in insulin signaling and glucose homeostasis (Knight et al. Cell (2006) 125(4): 733-47; Vanhaesebroeck et al. Current Topic Microbiol. Immunol. (2010) 347: 1-19). PI3K-β is activated in cancers where phosphatase and tensin homolog (PTEN) is deleted. Both isoforms are targets of small molecule therapeutics in development for cancer. There remains a need for improved therapy for cancers such as hematologic malignancies.

PI3K-δ and -γ are preferentially expressed in leukocytes and are important in leukocyte function. These isoforms also contribute to the development and maintenance of hematologic malignancies (Vanhaesebroeck et al. Current Topic Microbiol. Immunol. (2010) 347: 1-19; Clayton et al. J. Exp. Med. (2002) 196(6): 753-63; Fung-Leung Cell Signal (2011) 23(4): 603-8; Okkenhaug et al. Science (2002) 297(5583): 1031-34). PI3K-δ is activated by cellular receptors (e.g., receptor tyrosine kinases) through interaction with the Sarc homology 2 (SH2) domains of the PI3K regulatory subunit (p85), or through direct interaction with RAS.

Duvelisib is an inhibitor of PI3K with inhibitory activity predominantly against PI3K-δ and PI3K-γ isoforms expressed in normal and malignant B-cells. Duvelisib induced growth inhibition and reduced viability in cell lines derived from malignant B-cells and in primary CLL tumor cells. Duvelisib inhibits several key cell-signaling pathways, including B-cell receptor signaling and CXCR12-mediated chemotaxis of malignant B-cells. Additionally, duvelisib inhibits CXCL12-induced T cell migration and M-CSF and IL-4 driven M2 polarization of macrophages.

SUMMARY

Provided herein, at least in part, are methods of treating a hematologic malignancy in a human subject in need thereof, comprising orally administering to the subject duvelisib or a pharmaceutically acceptable form thereof.

Thus in one aspect, provided herein is a method of treating a hematologic malignancy in a human subject in need thereof, the method comprising:

(i) orally administering to the subject about 75 mg of duvelisib, or a pharmaceutically acceptable form thereof, twice daily for a first interval; and (ii) orally administering to the subject about 25 mg of duvelisib, or a pharmaceutically acceptable form thereof, twice daily for a second interval;

thereby treating the subject.

In another aspect, provided herein is a method of treating a hematologic malignancy in a human subject in need thereof, the method comprising:

(i) orally administering to the subject about 25 mg of duvelisib, or a pharmaceutically acceptable form thereof, twice daily for about 12 weeks; and a cycle comprising:

(ii) abstaining from orally administering duvelisib, or a pharmaceutically acceptable form thereof, for about 2 weeks; and (iii) orally administering to the subject about 25 mg of duvelisib, or a pharmaceutically acceptable form thereof, twice daily for about 2 weeks;

thereby treating the subject.

In some embodiments, the cycle is repeated at least once.

In another aspect, provided herein is a method of treating a hematologic malignancy in a human subject in need thereof, the method comprising a cycle comprising:

(i) orally administering to the subject about 25 mg of duvelisib, or a pharmaceutically acceptable form thereof, twice daily for about 2 weeks; and (ii) abstaining from orally administering duvelisib, or a pharmaceutically acceptable form thereof, for about 2 weeks;

thereby treating the subject.

In some embodiments, the cycle is repeated at least once.

In some embodiments, the hematologic malignancy is relapsed or refractory.

In some embodiments, the hematologic malignancy is chronic lymphocytic leukemia (CLL), small lymphocytic lymphoma (SLL), follicular lymphoma (FL), B-cell lymphoma, CLL/SLL, indolent non-Hodgkin lymphoma, mantle cell lymphoma, T-cell lymphoma, peripheral T-cell lymphoma, or cutaneous T-cell lymphoma. In some embodiments, the hematologic malignancy is peripheral T-cell lymphoma. In some embodiments, the hematologic malignancy is indolent non-Hodgkin lymphoma. In some embodiments, the hematologic malignancy is relapsed or refractory peripheral T-cell lymphoma. In some embodiments, the hematologic malignancy is relapsed or refractory indolent non-Hodgkin lymphoma.

DETAILED DESCRIPTION

The present invention provides, in part, methods of treating a hematologic malignancy in a human subject in need thereof, comprising orally administering to the subject duvelisib or a pharmaceutically acceptable form thereof.

Methods of Treatment

In an aspect, provided herein is a method of treating a hematologic malignancy in a human subject in need thereof, the method comprising:

(i) orally administering to the subject about 75 mg of duvelisib, or a pharmaceutically acceptable form thereof, twice daily for a first interval; and (ii) orally administering to the subject about 25 mg of duvelisib, or a pharmaceutically acceptable form thereof, twice daily for a second interval;

thereby treating the subject.

In some embodiments, the first interval is at least 4 weeks. In some embodiments, the first interval is about 8 weeks. In some embodiments, the first interval is 8 weeks.

In some embodiments, the second interval is at least 4 weeks.

In some embodiments, the method may further comprise increasing the dose of duvelisib or a pharmaceutically acceptable form thereof to about 75 mg twice daily subsequent to the second interval.

In some embodiments, the method may further comprise a rest period (i.e., abstaining from orally administering duvelisib or a pharmaceutically acceptable form thereof) between the first interval and the second interval. In some embodiments, the subject is identified as having an adverse effect during the first interval. In some embodiments, the adverse effect identified in the subject during the first interval is reduced or eliminated during the rest period.

In another aspect, provided herein is a method of treating a hematologic malignancy in a human subject in need thereof, the method comprising:

(i) orally administering to the subject about 25 mg of duvelisib, or a pharmaceutically acceptable form thereof, twice daily for about 12 weeks; and a cycle comprising:

(ii) abstaining from orally administering duvelisib, or a pharmaceutically acceptable form thereof, for about 2 weeks; and (iii) orally administering to the subject about 25 mg of duvelisib, or a pharmaceutically acceptable form thereof, twice daily for about 2 weeks;

thereby treating the subject.

In some embodiments, the cycle is repeated at least once.

In another aspect, provided herein is a method of treating a hematologic malignancy in a human subject in need thereof, the method comprising a cycle comprising:

(i) orally administering to the subject about 25 mg of duvelisib, or a pharmaceutically acceptable form thereof, twice daily for about 2 weeks; and (ii) abstaining from orally administering duvelisib, or a pharmaceutically acceptable form thereof, for about 2 weeks;

thereby treating the subject.

In some embodiments, the cycle is repeated at least once.

Duvelisib

Duvelisib has the following structure:

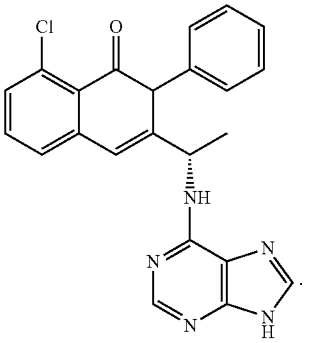 [SMILES: C[C@H](Nc1ncnc2[nH]cnc12)C1=Cc2cccc(Cl)c2C(=O)C1c1ccccc1]

In some embodiments, a polymorph of duvelisib may be used. Exemplary polymorphs are disclosed in U.S. Patent Publication No. 2012/0184568, which is hereby incorporated by reference in its entirety. Duvelisib can be synthesized according to exemplary methods disclosed in U.S. Patent Publication No. US 2009/0312319, International Patent Publication No. WO 2011/008302A1, and U.S. Patent Publication No. 2012/0184568, each of which is hereby incorporated by reference in its entirety, and/or according to methods known in the art. In some embodiments, a pharmaceutically acceptable form of duvelisib is a hydrate, a solvate, or a salt thereof.

Cancers and Hematologic Malignancies

The diseases or disorders (e.g., cancer or hematologic malignancy) that can be treated with duvelisib, or a pharmaceutically acceptable form thereof, or pharmaceutical composition thereof, or according to the methods as provided herein, include, but are not limited to, chronic lymphocytic leukemia (CLL), small lymphocytic lymphoma (SLL), follicular lymphoma (FL), B-cell lymphoma, CLL/SLL, indolent non-Hodgkin lymphoma, mantle cell lymphoma, T-cell lymphoma, peripheral T-cell lymphoma, and cutaneous T-cell lymphoma.

In some embodiments, the hematologic malignancy is chronic lymphocytic leukemia (CLL), small lymphocytic lymphoma (SLL), or follicular lymphoma (FL).

In some embodiments, the hematologic malignancy is peripheral T-cell lymphoma.

In some embodiments, the hematologic malignancy is indolent non-Hodgkin lymphoma.

Other contemplated diseases or disorders (e.g., cancer or hematologic malignancy) that can be treated with duvelisib, or a pharmaceutically acceptable form thereof, or pharmaceutical composition thereof, or according to the methods as provided herein, include, breast cancer such as a ductal carcinoma, lobular carcinoma, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone;

pancreatic cancer such as epithelioid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer; kidney cancer; thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and Burkitt lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), oligodendroglioma, ependymoma, meningioma, lymphoma, schwannoma, and medulloblastoma; peripheral nervous system (PNS) cancers such as acoustic neuromas and malignant peripheral nerve sheath tumor (MPNST) including neurofibromas and schwannomas, malignant fibrocytoma, malignant fibrous histiocytoma, malignant meningioma, malignant mesothelioma, and malignant mixed Miillerian tumor; oral cavity and oropharyngeal cancers such as, hypopharyngeal cancer, laryngeal cancer, nasopharyngeal cancer, and oropharyngeal cancer; stomach cancers such as lymphomas, gastric stromal tumors, and carcinoid tumors; testicular cancers such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin lymphoma, non-Hodgkin lymphomas carcinoids or carcinoid tumors; rectal cancer; and colon cancer.

In some embodiments, the cancer or disease is a blood disorder or a hematologic malignancy.

In some embodiments, the cancer or disease is selected from one or more of the following: acoustic neuroma, adenocarcinoma, adrenal gland cancer, anal cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarinoma), Ewing sarcoma, familiar hypereosinophilia, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphocytic leukemia (ALL), which includes B-lineage ALL and T-lineage ALL, chronic lymphocytic leukemia (CLL), prolymphocyte leukemia (PLL), hairy cell leukemia (HCL) and Waldenstrom's macroglobulinemia (WM); peripheral T cell lymphomas (PTCL), adult T cell leukemia/lymphoma (ATL), cutaneous T-cell lymphoma (CTCL), large granular lymphocytic leukemia (LGF), Hodgkin's disease and Reed-Stemberg disease; acute myelocytic leukemia (AML), chronic myelocytic leukemia (CIVIL), chronic lymphocytic leukemia (CLL)), lymphoma (e.g., Hodgkin lymphoma (HL), non-Hodgkin lymphoma (NHL), follicular lymphoma, diffuse large B-cell lymphoma (DLBCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic andenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenstrom's macroglobulinemia.

In some embodiments, the cancer or disease is a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others.

In some embodiments, the blood disorder or the hematologic malignancy includes, but is not limited to, acute lymphoblastic leukemia (ALL), T-cell ALL (T-ALL), B-cell ALL (B-ALL), acute myeloid leukemia (AML), chronic lymphocytic leukemia (CLL), chronic myelogenous leukemia (CIVIL), blast phase CIVIL, small lymphocytic lymphoma (SLL), CLL/SLL, blast phase CLL, Hodgkin lymphoma (HL), non-Hodgkin lymphoma (NHL), B-cell NHL, T-cell NHL, indolent NHL (iNHL), diffuse large B-cell lymphoma (DLBCL), mantle cell lymphoma (MCL), aggressive B-cell NHL, B-cell lymphoma (BCL), Richter's syndrome (RS), T-cell lymphoma (TCL), peripheral T-cell lymphoma (PTCL), cutaneous T-cell lymphoma (CTCL), transformed mycosis fungoides, Sezary syndrome, anaplastic large-cell lymphoma (ALCL), follicular lymphoma (FL), Waldenstrom macroglobulinemia (WM), lymphoplasmacytic lymphoma, Burkitt lymphoma, multiple myeloma (MM), amyloidosis, MPD, essential thrombocytosis (ET), myelofibrosis (MF), polycythemia vera (PV), chronic myelomonocytic leukemia (CMML), myelodysplastic syndrome (MDS), angioimmunoblastic lymphoma, high-risk MDS, and low-risk MDS. In some embodiments, the hematologic malignancy is relapsed. In some embodiments, the hematologic malignancy is refractory. In some embodiments, the cancer or disease is in a pediatric patient (including an infantile patient). In some embodiments, the cancer or disease is in an adult patient. Additional embodiments of a cancer or disease being treated or prevented by methods, compositions, or kits provided herein are described herein elsewhere.

In some embodiments, the hematologic malignancy is relapsed or refractory.

In some embodiments, the hematologic malignancy is relapsed or refractory peripheral T-cell lymphoma. In some embodiments, the hematologic malignancy is relapsed or refractory indolent non-Hodgkin lymphoma.

In some embodiments, the hematologic malignancy is relapsed or refractory CLL after at least two prior therapies. In some embodiments, the hematologic malignancy is relapsed or refractory SLL after at least two prior therapies. In some embodiments, the hematologic malignancy is relapsed or refractory FL after at least two prior therapies. In some embodiments, the hematologic malignancy is relapsed or refractory indolent non-Hodgkin lymphoma after at least one prior therapy. In some embodiments, the hematologic malignancy is relapsed or refractory peripheral T-cell lymphoma after at least one prior therapy.

The effectiveness of treatment in the preceding methods can for example be determined by measuring the decrease in size of tumors present in the patients with the neoplastic condition, or by assaying a molecular determinant of the degree of proliferation of the tumor cells.

Suitable test agents which can be tested in the preceding method include combinatorial libraries, defined chemical entities, peptide and peptide mimetics, oligonucleotides and natural product libraries, such as display (e.g., phage display libraries) and antibody products. Test agents may be used in an initial screen of, for example, 10 substances per reaction, and the substances of these batches which show inhibition or activation tested individually. Test agents may be used at a concentration of from 1 nM to 1000 μM, preferably from 1 μM to 100 μM, more preferably from 1 μM to 10 μM.

Dosing and Formulations

In some embodiments, duvelisib or a pharmaceutically acceptable form thereof may be administered daily, every other day, three times a week, twice a week, weekly, or bi-weekly. In some embodiments, duvelisib or a pharmaceutically acceptable form thereof is administered daily. In some embodiments, duvelisib or a pharmaceutically acceptable form thereof is administered twice daily (BID).

Administration of duvelisib or a pharmaceutically acceptable form thereof may continue as long as necessary. In some embodiments, duvelisib or a pharmaceutically acceptable form thereof is administered for more than about 1, about 2, about 3, about 4, about 5, about 6, about 7, about 14, about 28 days, or about 56 days. In some embodiments, duvelisib or a pharmaceutically acceptable form thereof is administered chronically on an ongoing basis (e.g., repeating cycles, as described herein, as necessary), e.g., for the treatment of chronic effects.

In some embodiments, duvelisib or a pharmaceutically acceptable form thereof is administered at an amount of about 10 mg to about 200 mg, about 20 mg to about 150 mg, or about 50 mg to about 150 mg per day. In some embodiments, duvelisib or a pharmaceutically acceptable form thereof is administered at an amount of about 10 mg, about 15 mg, about 20 mg, about 25 mg, about 30 mg, about 35 mg, about 40 mg, about 45 mg, about 50 mg, about 60 mg, about 75 mg, about 80 mg, or about 100 mg per administration. In some embodiments, duvelisib or a pharmaceutically acceptable form thereof is administered at an amount of 25 mg twice daily. In some embodiments, duvelisib or a pharmaceutically acceptable form thereof is administered at an amount of 50 mg twice daily. In some embodiments, duvelisib or a pharmaceutically acceptable form thereof is administered at an amount of 75 mg twice daily.

In some embodiments of the methods described herein, duvelisib or a pharmaceutically acceptable form thereof is administered orally. In some embodiments, duvelisib or a pharmaceutically acceptable form thereof is formulated as a pharmaceutical composition (e.g., a composition comprising duvelisib or a pharmaceutically acceptable form thereof and a pharmaceutical excipient(s)) suitable for oral administration. In some embodiments, duvelisib or a pharmaceutically acceptable form thereof is formulated as an oral dosage form (e.g., solid oral dosage form). In some embodiments, the composition or oral dosage form of duvelisib or a pharmaceutically acceptable form thereof is in the form of a capsule. In exemplary embodiments, the pharmaceutically acceptable excipient or carrier in the composition is one or more of microcrystalline cellulose (e.g., silicified microcrystalline cellulose), crospovidone, and/or magnesium stearate. In some embodiments, the pharmaceutically acceptable excipient or carrier in the composition is one or more of colloidal silicon dioxide, crospovidone, magnesium stearate, and microcrystalline cellulose. In some embodiments, capsule shells may contain gelatin, titanium dioxide, black ink, and red iron oxide.

Kits

In some embodiments, provided herein are kits. The kits may include a pharmaceutical composition as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information may be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" may be a single tablet or capsule or several tablets or capsules to be taken on a given day.

Suitable packaging and additional articles for use (e.g., measuring cup for liquid preparations, foil wrapping to minimize exposure to air, and the like) are known in the art and may be included in the kit. In other embodiments, kits may further comprise devices that are used to administer the active agents. Examples of such devices include, but are not limited to, syringes, drip bags, patches, and inhalers. Kits described herein may be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules may be removed from the blister pack by manually applying pressure on the recesses whereby an opening is formed in the sheet at the place of the recess. The tablet or capsule can then be removed via said opening.

Kits may further comprise pharmaceutically acceptable vehicles that may be used to administer one or more active agents. For example, if an active agent is provided in a solid form that must be reconstituted for parenteral administration, the kit can comprise a sealed container of a suitable vehicle in which the active agent may be dissolved to form a particulate-free sterile solution that is suitable for parenteral administration. Examples of pharmaceutically acceptable vehicles include, but are not limited to: Water for Injection USP;

aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Combination Therapy

In some embodiments, duvelisib or a pharmaceutically acceptable form thereof may be administered in combination with one or more other therapies.

By "in combination with," it is not intended to imply that the other therapy and duvelisib or a pharmaceutically acceptable form thereof must be administered at the same time and/or formulated for delivery together, although these methods of delivery are within the scope of this disclosure. Duvelisib or a pharmaceutically acceptable form thereof can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other therapies (e.g., one or more other additional agents). In general, each therapeutic agent will be administered at a dose and/or on a time schedule determined for that particular agent. The other therapeutic agent can be administered with duvelisib or a pharmaceutically acceptable form thereof in a single composition or separately in a different composition. Triple therapy is also contemplated herein.

In general, it is expected that additional therapeutic agents employed in combination be utilized at levels that do not exceed the levels at which they are utilized individually. In some embodiments, the levels utilized in combination will be lower than those utilized individually.

In some embodiments, duvelisib or a pharmaceutically acceptable form thereof is a first line treatment for cancer or hematologic malignancy, i.e., it is used in a subject who has not been previously administered another drug or therapy intended to treat cancer or hematologic malignancy or one or more symptoms thereof.

In other embodiments, duvelisib or a pharmaceutically acceptable form thereof is a second line treatment for cancer or hematologic malignancy, i.e., it is used in a subject who has been previously administered another drug or therapy intended to treat cancer or hematologic malignancy or one or more symptoms thereof.

In other embodiments, duvelisib or a pharmaceutically acceptable form thereof is a third or fourth line treatment for cancer or hematologic malignancy, i.e., it is used in a subject who has been previously administered two or three other drugs or therapies intended to treat cancer or hematologic malignancy or one or more symptoms thereof.

In some embodiments where two agents are administered, the agents can be administered in any order. For example, the two agents can be administered concurrently (i.e., essentially at the same time, or within the same treatment) or sequentially (i.e., one immediately following the other, or alternatively, with a gap in between administration of the two). In some embodiments, duvelisib or a pharmaceutically acceptable form thereof is administered sequentially (i.e., after the first therapeutic), In some embodiments, other therapy includes, but is not limited to, chemotherapeutic agents, therapeutic antibodies, and/or radiation treatment, which is administered in combination with duvelisib or a pharmaceutically acceptable form thereof to provide a synergistic or additive therapeutic effect.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (imatinib mesylate), Velcade®

(bortezomib), Casodex™ (bicalutamide), Iressa® (gefitinib), Tarceva® (erlotinib), and Adriamycin® (doxorubicin) as well as a host of chemotherapeutic agents. Non-limiting examples of chemotherapeutic agents include alkylating agents such as thiotepa and cyclosphosphamide (CYTOXAN™), alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; BTK inhibitors such as ibrutinib (PCI-32765); AVL-292, Dasatinib, LFM-AI3, ONO-WG-307, and GDC-0834; HDAC inhibitors such as vorinostat, romidepsin, panobinostat, valproic acid, belinostat, mocetinostat, abrexinostat, entinostat, SB939, resminostat, givinostat, CUDC-101, AR-42, CHR-2845, CHR-3996, 4SC-202, CG200745, ACY-1215 and kevetrin; EZH2 inhibitors such as, but not limited to, EPZ-6438 (N-((4,6-dimethyl-2-oxo-1,2-dihydropyridin-3-yl)methyl)-5-(ethyl(tetrahydro-2H-pyran-4-yl)amino -4-methyl-4'-(morpholinomethyl)-[1,1'-biphenyl]-3- carboxamide), GSK-126 ((S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide), GSK-343 (1-Isopropyl-N-((6-methyl-2-oxo-4-propyl-1,2-dihydropyridin-3-yl)methyl)-6-(2-(4-methylpiperazin-1-yl)pyridine-4- yl)-1H-indazole-4-carboxamide), E11, 3-deazaneplanocin A (DNNep, 5R-(4-amino-1H-imidazo[4,5-c]pyridin-1-yl)-3-(hydroxymethyl)-3-cyclopentene-1S,2R-diol), small interfering RNA (siRNA) duplexes targeted against EZH2 (S. M. Elbashir et al., Nature 411: 494-498 (2001)), isoliquiritigenin, and those provided in, for example, U.S. Publication Nos. 2009/0012031, 2009/0203010, 2010/0222420, 2011/0251216, 2011/0286990, 2012/0014962, 2012/0071418, 2013/0040906, and 2013/0195843; JAK/STAT inhibitors such as lestaurtinib, tofacitinib, ruxolitinib, pacritinib, CN1387, baricitinib, GLPG0636, TG101348,INCB 16562, CP-690550, and AZD1480; PKC-β inhibitor such as Enzastaurin; SYK inhibitors such as, but not limited to, GS-9973, 8788 (fostamatinib), PRT 062607, R406, (S)-2-(2-((3,5-dimethylphenyl)amino)pyrimidin-4-yl)-N-(1-hydroxypropan-2-yl)-4-methylthiazole-5- carboxamide, R11 2, GSK143, BAY61-3606, PP2, PRT 060318, R348, and those provided in, for example; U.S. Publication Nos. 2003/0113828, 2003/0158195, 2003/0229090, 2005/0075306, 2005/0232969, 2005/0267059, 2006/0205731, 2006/0247262, 2007/0219152, 2007/0219195, 2008/0114024; 2009/0171089, 2009/0306214, 2010/0048567, 2010/0152159, 2010/0152182, 2010/0316649, 2011/0053897, 2011/0112098, 2011/0245205, 2011/0275655, 2012/0027834, 2012/0093913, 2012/0101275, 2012/0130073; 2012/0142671, 2012/0184526, 2012/0220582, 2012/0277192, 2012/0309735, 2013/0040984, 2013/0090309, 2013/0116260, and 2013/0165431, compounds of which are incorporated herein by reference; SYK/JAK dual inhibitor such as PRT2070, nitrogen mustards such as bendamustine; chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pralatrexate, pteropterin, trimetrexate; purine analogs such as fludarabine, 6-mercaptopurine, thiamiptine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™, razoxane; sizofiran; spirogermanium; tenuazonic acid; triaziquone, 2,2',2"-trichlorotriethyla-mine; urethan; vindesine; dacarbazine; mannomustine; mitobronitol; mitolactol; pipobroman; gacytosine; arabinoside (Ara-C); cyclophosphamide; thiotepa; taxanes, e.g., paclitaxel (e.g., TAXOL™) and docetaxel (e.g., TAXOTERE™) and ABRAXANE® (paclitaxel protein-bound particles); retinoic acid; esperamicins; capecitabine; and pharmaceutically acceptable forms (e.g., pharmaceutically acceptable salts, hydrates, solvates, isomers, prodrugs, and isotopically labeled derivatives) of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT- 11); topoisomerase inhibitor RFS 2000; difluoromethylornithine (DMFO). Where desired, duvelisib or a pharmaceutically acceptable form thereof can be used in combination with commonly prescribed anti-cancer drugs such as Herceptin®, Avastin®, Erbitux®, Rituxan®, Taxol®, Arimidex®, Taxotere®, ABVD, AVI CINE, abagovomab, acridine carboxamide, adecatumumab, 17-N-allylamino-17-demethoxygeldanatnycin, alpharadin, alvocidib, 3-aminopyridine-2-carhoxaldehyde thiosemicarbazone, amonafide, anthracenedione, anti-CD22 immunotoxins, antineoplastic, antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, crizotinib, cell-cycle non-specific antineoplastic agents, dichloroacetic acid, discodermolide, elsamitrucin, enocitabine, epothilone, eribulin, everolimus, exatecan, exisulind, ferruginol, forodesine, fosfestrol, ICE chemotherapy regimen, IT-101, imexon imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitor, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and disclosed in U.S. Pat. No. 7,230,004, U.S. Patent Application Publication No. 2008/0293754, U.S. Patent Application Publication No. 2008/0287420, and U.S. Patent Application Publication No. 2008/0293755. Examples of other suitable hedgehog inhibitors include those described in U.S. Patent Application Publication Nos. US 2002/0006931, US 2007/0021493 and US 2007/0060546, and International Application Publication Nos, WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/1 1061 1, WO 2008/112913, and WO 2008/131354, compounds of which are incorporated herein by reference. Additional examples of hedgehog inhibitors include; but are not limited to, GDC-0449 (also known as RG3616 or vismodegib) described in, e.g., Von Hoff D. et al:, N. Engl. J. Med. 2009; 361(12): 1164-72; Robarge K. D. et al., Bioorg Med Chem Lett. 2009; 19(19):5576-81 Yauch, R. L. et al. (2009) Science 326: 572-574; Sciencexpress: 1-3 (10.1126/science. 1 179386); Rudin, C. et al. (2009) New England J of Medicine 361-366 (10.1056/nejma0902903); BMS-833923 (also known as XL139) described in, e.g., in Siu L. et al., J. Clin. Oncol. 2010; 28: 15s (suppl; abstr 2501); and National Institute of Health Clinical Trial Identifier No. NCT006701891; LDE-225 described, e.g., in Pan S. et al., ACS Niled, Chem. Lett, 2010; 1(3): 130-134; LEQ-506 described, e.g., in National Institute of Health Clinical Trial Identifier No. NCT01106508; PF-04449913 described, in National Institute of Health Clinical Trial Identifier No. NCT00953758; Hedgehog pathway antagonists disclosed in U.S. Patent Application Publication No. 2010/02861 14; SMOi2-17 described, e.g., U.S. Patent Application Publication No. 2010/0093625; SANT-1 and SANT-2 described, e.g., in Rominger C. M. et al.; Pharmacol. Exp. Ther. 2009; 329(3):995-1005; 1-piperazinyl-4-arylphthalazines or analogues thereof, described in Lucas B. S. et al., Bioorg. Med. Chem. Lett. 2010; 20(12):3618-22.

Other hormonal therapy and chemotherapeutic agents include, but are not limited to, anti-estrogens (e.g. tamoxifen, raloxifene, and megestrol acetate), LHRH agonists (e.g. goserelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estrarnustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids or taxanes (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG-1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoitinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, raltitrexed, tegafur-uracil, capecitabine), cytosine analogs (e.g. cytarabine (ara C, cytosine arabinoside), and fludarabine), purine analogs (e.g. mercaptopurine and thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracyclines (e.g. daunonibicin, doxorubicin, pegylated liposomal doxorubicin, idarubicin, epirubicin; pirarubicin, zorubicin, mitoxantrone), MDR inhibitors (e.g. verapamil), Ca2+ ATPase inhibitors (e.g. thapsigargin), thalidomide, lenalidomide (REVLIMID®), tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®,), cetuximab (ERBITUX®), panitumumab (VECTIBIX®), ranibizumab (Lucentis®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib AV-951 OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbazine, prednisolone, dexamethasone, camptothecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Exemplary biotherapeutic agents include, but are not limited to, interferons, cytokines (e.g., tumor necrosis factor, interferon a, interferon γ), vaccines, hematopoietic growth factors, monoclonal serotherapy, immuno-stimulants and/or immuno-modulatory agents (e.g., IL-1, 2, 4, 6, or 12), immune cell growth factors (e.g., GM-CSF) and antibodies (e.g. Herceptin (trastuzutnab), T-DM1, AVASTIN (bevacizumab), ERBITUX (cetuximab), Vectibix (panitumumab), Rituxan (rituximab), Bexxar (tositumomab), or Perjeta (pertuzumab)).

In one embodiment, the biotherapeutic agent is an anti-CD37 antibody such as, but not limited to, IMGN529, K7153A and TRU-016. In another embodiment, the biotherapeutic agent is an anti-CD20 antibody such as, but not limited to, $^{131}$I tositumomab, $^{90}$Y ibritumomab, $^{111}$I ibritumomab, obinutuzumab and ofatumumab. In another embodiment, the biotherapeutic agent is an anti-CD52 antibody such as, but not limited to, alemtuzumab.

In some embodiments, the chemotherapeutic is selected from HSP90 inhibitors. The HSP90 inhibitor can be a geldanamycin derivative, e.g., a benzoquinone or hygroquinone ansamycin HSP90 inhibitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT-129397, PU-H71, or PF-04928473 (SNX-2112).

In some embodiments, the chemotherapeutic is selected from PI3K inhibitors including those P13K inhibitors provided herein and those PI3K inhibitors not provided herein). In some embodiment, the PI3K inhibitor is an inhibitor of delta and gamma isoforms of P13K. In some embodiment, the P13K inhibitor is an inhibitor of delta isoform of PI3K. In some embodiment, the PI3K inhibitor is an inhibitor of gamma isoform of PI3K. In some embodiments, the PI3K inhibitor is an inhibitor of alpha isoform of PI3K. In other embodiments, the PI3K inhibitor is an inhibitor of one or more alpha, beta, delta and gamma isoforms of PI3K. Exemplary PI3K inhibitors that can be used in combination are described in, e.g., WO 09/088990, WO 09/088086, WO 2011/008302, WO 2010/036380, WO 2010/006086, WO 09/114870, WO 05/113556; US 2009/0312310, and US 2011/0046165, compounds of which are incorporated herein by reference. Additional PI3K inhibitors that can be used in combination with the pharmaceutical compositions, include but are not limited to, AMG-319, GSK 2126458, GDC-0980, GDC-0941, Sanofi XL147, XL499, XL756, XL147, PF-4691502, BKM 120, CAL-101 (GS-1101), CAL 263, SF1126, PX-886; and a dual PI3K inhibitor (e.g., Novartis BEZ235). In one embodiment, the PI3K (inhibitor is an isoquinolinone.

In some embodiments, the chemotherapeutic is selected from polo-like kinase 1 (PLK1) inhibitors such as, but not limited to, volasertib (B16727: N-((1S,4S)-4-(4-(cyclopropylmethyl)piperazin-1-yl)cyclohexyl)-4-(((R)-7- ethyl-8-isopropyl-5- methyl-6-oxo-5,7,8-tetrahydropteridin-2-yl) amino)-3-methoxybenzamide), BI2536 ((R)-4-[(8-Cyclopentyl-7-ethyl-5,6,7,8-tetrahydro-5-methyl-6-oxo-2-pteridinyl)amino]-3-methoxy-N-(1-methyl-4- piperidinyl) benzamide), ZK-Thiazolidone ((2-imidazol-1-yl-1-oxidanyl-1-phosphono-ethyl)phosphonic acid), TAK-960 (4-((9-cyclopentyl-7,7-difluoro-5-methyl-6-oxo-6,7,8,9-tetrahydro-5H-pydmido[4,5-b][1,4]diazepin-2- yl)amino)-2-fluoro-5-methoxy- N-(1-methylpiperidin-4-yl)benzamide), MLN0905 (2-((5-(3-(dimethylamino)propyl)-2-methylpyridin-3-yl)amino)-9-(trifluoromethyl)-5H-benzo[b]pyrimido [4,5-d]azepine- 6(7H)-thione), GSK461364 ((R)-5-(6-((4-methylpiperazin-1-yl)methyl)-1H-benzo[d]imidazol-1-yl)-3-(1-(2-(trifluoromethyl)phenyl)ethoxy)thiophene-2-carboxamide), rigosertib (ON-01910; sodium (E)-2-((2-methoxy-5-(((2,4,6-trimethoxystyryl)sulfonyl)methyl) phenyl)amino)acetate) and FLMN-214 ((H)-4-(2-(N-((4-methoxyphenyl)sulfonyl)acetamido)styryl)pyridine 1-oxide).

In some embodiments, the chemotherapeutic is selected from IRAK, inhibitors. Inhibitors of the IRAK protein kinase family refer to compounds which inhibit the function of IRAK protein kinases and more preferably compounds which inhibit the function of IRAK-4 and/or IRAK-1. Exemplary IRAK inhibitors include, but are not limited to, IRAK4 inhibitors such as ND-2110 and ND-2158; the IRAK inhibitors disclosed in WO2003/030902, WO2004/041285, WO2008/030579, and Buckley et al. (IRAK-4 inhibitors. Part 1: a series of amides. In Bioorganic & medicinal chemistry letters 2008, 18(11):3211-3214; IRAK-4 inhibitors. Part II: a structure-based assessment of imidazo[1,2-a] pyridine binding. In Bioorganic & medicinal chemistry letters 2008, 18(11):3291-3295; IRAK-4 inhibitors. Part 111: a series of imidazo[1,2-a]pyridines. In Bioorganic & medicinal chemistry letters 2008, 18(11):3656-3660); RO6245, RO0884, N-acyl 2-aminobenzimi dazoles 1-(2-(4-Morpholinypethyl)-2-(3- nitrobenzoylamino)benzimidazole, and/or N-(2-Morpholinylethyl)-2-(3-nitrobenzoylamido)-benzimidazole.

In some embodiments, radiation therapy can be administered through one of several methods, or a combination of methods, including without limitation, external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, 1-131, 1-125, Y-90, Re-186, Re-188, Sm-153, Bi-212, P-32, and radioactive isotopes of Lu). Suitable radiation sources for use as a cell conditioner as provided herein include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of 1-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, duvelisib or a pharmaceutically acceptable form thereof may render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of duvelisib or a pharmaceutically acceptable form thereof which amount is effective in sensitizing abnormal cells to treatment with radiation. The amount of 7 duvelisib or a pharmaceutically acceptable form thereof used in this method can be determined according to the means for ascertaining effective amounts of duvelisib or a pharmaceutically acceptable form thereof.

In some embodiments, provided herein is a method for using duvelisib or a pharmaceutically acceptable form thereof in combination with surgery.

In one embodiment, duvelisib or a pharmaceutically acceptable form thereof can be used in combination with an amount of one or more substances selected from anti-angiogenesis agents, signal transduction inhibitors, and anti-proliferative agents, glycolysis inhibitors, or autophagy inhibitors.

Other therapeutic agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with duvelisib or a pharmaceutically acceptable form thereof. Such therapeutic agents include, for example, rapamycin, temsirolimus (CO-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published October 21, 1999), WO 99/29667 (published Jun. 17, 1999), PCT International Application No. PCT/IB98/01113 (filed Jul. 21, 1998), European Patent Application No, 99302232,1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997). In some embodiments, MMP-2 and MMP-9 inhibitors are those that have little or no activity inhibiting MMP-1. Other embodiments include those that selectively inhibit MMP-2 and/or AMP-9 relative to the other matrix-metalloproteinases (e.g., MAP-1, MMP-4, MMP-5, MMP-6, MMP-7, MMP-8, MMP-10, MMP-11, MMP-12, and MMP-13). Some non-limiting examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilotnycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine, In addition, antisense or siRNAs that inhibit expression of proteins including, but not limited to ATC15 (which are implicated in autophagy), can also be used.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived. autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Examples of therapeutic antibodies that can be combined with duvelisib or a pharmaceutically acceptable form thereof include but are not limited to anti-receptor tyrosine kinase antibodies (cetuximab, panitumumab, trastuzumab), anti CD20 antibodies (rituximab, tositumomab), and other antibodies such as alemtuzutnab, bevacizutnab, and gemtuzumab.

Moreover, therapeutic agents used for immuno-modulation, such as immuno-modulators, immuno-suppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and anti-platelet drugs are also contemplated by the methods herein.

In other embodiments, duvelisib or a pharmaceutically acceptable form thereof may be administered in combination with a MEK inhibitor. In one embodiment, the MEK inhibitor is tametinib/GSK1120212 (N-(3-{3-Cyclopropyl-5-[(2-fluoro-4-iodophenyl)amino]-6,8-dimethyl-2,4,7-trioxo-3,4,6,7- tetrahydropyrido[4,3-d]pyrimidin-l(2H)-yl}phenyl) acetamide), selumetinob (6-(4-bromo-2-chloroanilino)-7-fluoro-N-(2-hydroxyethoxy)-3-methylbenzimidazole-5-carboxamide), pimasertib/AS703026/MSC 1935369 ((S)-N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1- sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpytido[2,3-d]pyrimidine-4,7(3H,8H)- dione) MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/

CH4987655 (3,4-difluoro-2-((2-fluoro-4-iodophenyl) amino)-N-(2-hydroxyethoxy)-5-((3-oxo-1,2-oxazinan-2-yl)methyl)benzamide), or AZD8330 (2-((2-fluoro-4-iodo-phenyl)amino)-N-(2-hydroxyethoxy)-1,5-dimethyl-6-oxo-1,6-dihydropyridine-3-carboxamide).

In other embodiments, duvelisib or a pharmaceutically acceptable form thereof may be administered in combination with a bcl-2 inhibitor. In one embodiment, the BCL2 inhibitor is ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H- pyran-4-yl)methyl]amino]phenyl] sulfonyl]-2-[(1H-pyrrolo[2,3-b]pyridin-5-yl)oxy] benzamide), ABT-737 (4-[4-[[2-(4-chlorophenyl)phenyl] methyl]piperazin-1-yl]-N-[4-[[(2R)-4-(dimethylamino)-1-phenylsulfanylbutan-2-yl]amino]-3-nitrophenyl] sulfonylbenzamide), ABT-263 ((R)-4-(4-((4'-chloro-4,4-dimethyl-3,4,5,6-tetrahydro-[1,1'-biphenyl]-2-yl)methyl) piperazin-1-yl)-N-((4-((4- morpholino-1-(phenylthio)butan-2-yl)amino)-3((trifluoromethyl)sulfonyl)phenyl)sulfonyl) benzamide), GX15-070 (obatoclax mesylate, (2Z)-2-[(5Z)-5-[(5-dimethyl-1H-pyrro1-2-yl)methylidene]-4-methoxy-pyrrol-2-ylidene]indole; methanesulfonic acid))), or G3139 (Oblimersen).

Definitions

Unless defined otherwise, all technical and scientific terms used herein have the same meaning as is commonly understood by one of skill in the art to which this specification pertains.

As used herein, and unless otherwise indicated, the term “about” or “approximately” means an acceptable error for a particular value as determined by one of ordinary skill in the art, which depends in part on how the value is measured or determined. In some embodiments, the term “about” or “approximately” means within 1, 2, 3, or 4 standard deviations. In some embodiments, the term “about” or “approximately” means within 50%, 20%, 15%, 10%, 9%, 8%, 7%, 6%, 5%, 4%, 3%, 2%, 1%, 0.5%, or 0.05% of a given value or range.

As used herein, the terms “treatment” and “treating” are used herein to refer to an approach for obtaining beneficial or desired results including, but not limited to, therapeutic benefit. A therapeutic benefit includes, but is not limited to, eradication, inhibition, reduction, or amelioration of the underlying disorder being treated. Also, a therapeutic benefit is achieved with the eradication, inhibition, reduction, or amelioration of one or more of the physiological symptoms associated with the underlying disorder such that an improvement is observed in the patient, notwithstanding that the patient can still be afflicted with the underlying disorder.

The phrase “a method of treating” or its equivalent, when applied to, for example, cancer refers to a procedure or course of action that is designed to reduce or eliminate the number of cancer cells in an animal, or to alleviate the symptoms of a cancer. “A method of treating” cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

“Subject” or “patient” to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term “cancer” includes, but is not limited to, solid tumors and blood born tumors.

The term “cancer” refers to disease of skin tissues, organs, blood, and vessels, including, but not limited to, cancers of the bladder, bone or blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus.

Hematopoietic origin refers to involving cells generated during hematopoiesis, a process by which cellular elements of blood, such as lymphocytes, leukocytes, platelets, erythrocytes and natural killer cells are generated. Cancers of hematopoietic origin includes lymphoma and leukemia.

Resistant or refractory refers to when a cancer that has a reduced responsiveness to a treatment, e.g., up to the point where the cancer does not respond to treatment. The cancer can be resistant at the beginning of treatment, or it may become resistant during treatment. The cancer subject may have one or more mutations that cause it to become resistant to the treatment, or the subject may have developed such mutations during treatment. The term “refractory” can refer to a cancer for which treatment (e.g., chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

“Responsiveness,” to “respond” to treatment, and other forms of this term, as used herein, refer to the reaction of a subject to treatment with a therapeutic. Responsiveness to a therapy can be evaluated by using any of the alterations/biomarkers disclosed herein and/or comparing a subject's response to the therapy using one or more clinical criteria, such as IWCLL 2008 (for CLL) described in, e.g., Hallek, M. et al. (2008) Blood 111(12): 5446-5456; RECIST criteria for solid tumors (Response Evaluation Criteria In Solid Tumors), and the like. Additional classifications of responsiveness are provided in Brown, J. R. (2014) Blood, 123 (22): 3390-3397 and Chesson, B .D. et al. Journal of Clinical Oncology, 30(23): 2820-2822. These criteria provide a set of published rules that define when cancer patients improve (“respond”), stay the same (“stable”) or worsen (“progression”) during treatments.

In another embodiment in solid tumors, a subject responds to treatment with duvelisib or a pharmaceutically acceptable form thereof if growth of a tumor in the subject is retarded about 10%, 20%, 30%, 40%, 50%, 60%, 70%, 80%, 90% or more. In another example, a subject responds to treatment with duvelisib or a pharmaceutically acceptable form thereof if a tumor in the subject shrinks by about 5%, 10%, 20%, 30%, 40%, 50% or more as determined by any appropriate measure, e.g., by mass or volume. In another example, a subject responds to treatment with duvelisib or a pharmaceutically acceptable form thereof if the subject experiences a life expectancy extended by about 5%, 10%, 20%, 30%, 40%, 50% or more beyond the life expectancy predicted if no treatment is administered. In another example, a subject responds to treatment with duvelisib or a pharmaceutically acceptable form thereof if the subject has an increased disease-free survival, overall survival or increased time to progression. Several methods can be used to determine if a patient responds to a treatment including the RECIST criteria, as set forth above.

An "adverse event" (AE) as used herein refers to an untoward medical occurrence in a patient administered a medicinal product that does not necessarily have a causal relationship with this treatment. An AE can, therefore, be any unfavorable and unintended sign (including an abnormal laboratory finding), symptom, or disease temporally associated with the use of a medicinal (investigational) product, whether or not related to the study (investigational) product. This includes an exacerbation of pre-existing conditions or events, concurrent illnesses, drug interaction, or the significant worsening of the indication under investigation. Anticipated fluctuations of pre-existing conditions, including the disease under study that does not represent a clinically significant exacerbation or worsening, need not be considered AEs.

A "serious adverse event" (SAE) as used herein refers to an untoward medical occurrence at any dose (including after the ICF is signed and prior to dosing) that: results in death; is life-threatening (patient is at immediate risk of death from the event as it occurred); requires inpatient hospitalization (formal admission to a hospital for medical reasons) or prolongation of existing hospitalization; results in persistent or significant disability/incapacity; or results in a congenital anomaly/birth defect.

Chemical Definitions

As used herein, a "pharmaceutically acceptable form" of duvelisib includes, but is not limited to, pharmaceutically acceptable salts, hydrates, solvates, isomers, prodrugs, and isotopically labeled derivatives of duvelisib. In some embodiments, a "pharmaceutically. acceptable form" includes, but is not limited to, pharmaceutically acceptable salts, isomers, prodrugs and isotopically labeled derivatives of duvelisib. In some embodiments, the pharmaceutically acceptable form of duvelisib is pharmaceutically acceptable salts, hydrates, solvates thereof.

In some embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J Pharmaceutical Sciences (1977) 66: 1-19. Pharmaceutically acceptable salts of duvelisib may include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethane sulfonate, formate, fumarate, glucoheptonate, glycerophosphate, gluconate, hemisulfate, heptanoate, hexanoate, hydroiodide, 2-hydroxy-ethane sulfonate, lactobionate, lactate, laurate, lauryl sulfate, malate, maleate, malonate, methanesulfonate, 2-naphthalene sulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluene sulfonate, undecanoate, valerate salts, and the like. In some embodiments, organic acids from which salts may be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Organic bases from which salts may be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In some embodiments, the pharmaceutically acceptable form is a solvate (e.g., a hydrate). As used herein, the term "solvate" refers to compounds that further include a stoichiometric or non-stoichiometric amount of solvent bound by non-covalent intermolecular forces. The solvate may be of duvelisib or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, about 3 or about 4, solvent or water molecules.

In some embodiments, the pharmaceutically acceptable form is a prodrug. As used herein, the term "prodrug" refers to compounds that are transformed in vivo to yield duvelisib. A prodrug may be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et at, "Pro-drugs as Novel Delivery Systems," A. C. S. Symposium Series, Vol. 14, Chp 1, pp 1-12 and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure.

EXAMPLES

The representative examples that follow are intended to help illustrate the invention, and are not intended to, nor should they be construed to, limit the scope of the invention.

Example 1. Efficacy and Safety of Duvelisib in Patients with Relapsed or Refractory Peripheral T-Cell Lymphoma To achieve both a rapid remission and ameliorate longer-term toxicities, the dosage will be 75 mg BID until the first response assessment (2 cycles=56 days) at which the dose will be reduced to 25 mg BID. A proactive decrease in the dose is justified since the 25 mg BID dosage can be active in PTCL and later-onset toxicities may be prevented.

A oral dosage of 75 mg BID for the first 2 cycles (cycle=28 days) until the first response assessment, followed by a mandatory reduction to 25 mg BID thereafter and administered in 28-day cycles for those patients with complete response (CR), partial response (PR), or stable disease (SD), will be used. If a subsequent assessment demonstrates progression and the patient did not require a dose modification due to toxicity, the dose can be re-escalated to 75 mg BID with a confirmatory scan after approximately 4 weeks of therapy. If the patient has progressive disease at the confirmatory scan, then the patient should be discontinued. Patients that re-escalate to 75 mg BID may remain at this dose level until the need for dose modification or the criteria for discontinuation is met.

The primary objective of this study is to determine the efficacy of duvelisib at an optimal dose in patients with R/R PTCL.

The primary endpoint is objective response rate (ORR [CR+PR]), according to Lugano criteria (Cheson et al, J Clin Oncol 2014; 32(27):3059-3067) as assessed by Independent Review Committee (IRC).

Secondary endpoints include duration of response (DOR), for those patients with CR or PR, defined as the time from the first documentation of response to the first documentation of progressive disease (PD), or death due to any cause, treatment-emergent adverse events (TEAEs) and changes in laboratory values, PFS, defined as the time from the first study drug dose to the first documentation of PD, or death from any cause, disease control rate (DCR), defined as CR+PR+stable disease≥8 weeks, overall survival (OS), and PK parameters derived from blood concentrations of duvelisib and its metabolites.

Exploratory endpoints include analysis of PTCL tumor pharmacodynamic markers, analysis of PTCL tumor prognostic markers and analysis of cytokines and non-tumor immune populations Inclusion criteria:

1. ≥18 years of age
2. Pathologically-confirmed PTCL, as defined by the World Health Organization. Slides must be submitted for central pathology review. Results of central pathology review are not required prior to initiation of treatment.
3. Received at least 2 cycles of one standard regimen for newly diagnosed advanced PTCL, and one of the following:
   (a) failed to achieve at least a partial response after 2 or more cycles of standard therapy;
   (b) failed to achieve a complete response after completion of standard therapy; and/or
   (c) persistent or progressive disease after an initial response
4. For patients with CD30+ anaplastic large cell lymphoma (ALCL), failed or are ineligible or intolerant to brentuximab vedotin
5. Measurable disease as defined by Lugano (Cheson et al, J Clin Oncol 2014; 32(27):3059-3067) for PTCL, i.e., at least 1 measurable disease lesion>1.5 cm in at least one dimension by conventional techniques (18FDG-PET-CT, CT with contrast, MRI)
6. Must have the following laboratory parameters:
   Hemoglobin≥8.0 g/dL with or without transfusion support
   Platelet count≥25×109/L
   Serum creatinine≤2.0×the upper limit of normal (ULN)
   Total bilirubin≤1.5×ULN (in patients with Gilbert's Syndrome a bilirubin>1.5×ULN may be allowed)
   Aspartate aminotransferase (AST) and alanine aminotransferase (ALT)≤3.0×ULN
   CD4 lymphocyte count≥50/mm3 (0.05×109/L)
7. Eastern Cooperative Oncology Group (ECOG) performance status≤2
8. Recovery to≤Grade 1 or baseline for any toxicities due to prior treatments, with the exception of peripheral neuropathy (recovery to ≤Grade 2) or alopecia
9. Washout of at least 14 days or 5 half-lives, whichever is longer, from PTCL-directed therapy. If previously treated with lenalidomide, must have completed treatment 4 weeks prior to C1D1.
10. For women of childbearing potential (WCBP): negative serum β-human chorionic gonadotropin (β-hCG) pregnancy test within 1 week before first treatment (WCBP defined as a sexually mature woman who has not undergone surgical sterilization or who has not been naturally post-menopausal for at least 12 consecutive months for women>55 years of age)
11. Male and female patients of reproductive potential (i.e., not surgically sterile or female patients who are not postmenopausal) must be willing to use a highly effective method of contraception for the duration of study treatment and for at least 3 months after the last dose of duvelisib Exclusion Criteria:

1. Primary leukemic PTCL subtypes (i.e., T-cell prolymphocytic leukemia, T-cell large granular lymphocytic leukemia, adult T-cell leukemia/lymphoma and aggressive NK-cell leukemia) or transformed mycosis fungoides 2. Received prior allogeneic transplant
3. Received prior treatment with a phosphoinositide-3-kinase (PI3K) inhibitor
4. Major surgery within 4 weeks prior to Screening
5. Known central nervous system involvement by PTCL
6. Infection with hepatitis B, hepatitis C, human immunodeficiency virus (HIV) or human T-lymphotropic virus type 1. (Patients with a positive hepatitis B surface antigen [HBsAg] or hepatitis C antibody [HCVAb] will be excluded. Patients with a positive hepatitis B core antibody [HBcAb] must have negative hepatitis B virus [HBV] deoxyribonucleic acid (DNA) to be eligible, must receive prophylaxis with entecavir [or equivalent] concomitant with duvelisib treatment, and must be periodically monitored for HBV reactivation by institutional guidelines. Investigators who strongly believe that a positive HBcAb is false due to passive immunization from previous immunoglobulin infusion therapy should discuss the potential to defer HBV prophylaxis with the Medical Monitor.)
7. Active cytomegalovirus (CMV) infection (patients with detectable viral load)
8. History of tuberculosis treatment within 2 years prior to C1D1
9. History of chronic liver disease, veno-occlusive disease, or alcohol abuse
10. Ongoing treatment with chronic immunosuppressants (e.g., cyclosporine) or systemic steroids>20 mg of prednisone (or equivalent) once daily (QD)
11. Ongoing treatment for systemic bacterial, fungal, or viral infection at Screening
12. Administration of a live vaccine within 6 weeks of C1D1
13. Concurrent administration of medications or foods that are strong inhibitors or inducers of cytochrome P450 3A (CYP3A)
14. Unable to receive prophylactic treatment for pneumocystis at Screening
15. Baseline left ventricular ejection fraction (LVEF) <50% (or below institution's normal limit)
16. Baseline QT interval corrected with Fridericia's method (QTcF)>480 ms
17. Prior surgery or condition with gastrointestinal dysfunction that may significantly affect drug absorption (e.g., gastric bypass surgery, gastrectomy, etc., see Section 5.2)
18. If female, pregnant or breastfeeding
19. Concurrent active malignancy other than nonmelanoma skin cancer, carcinoma in situ of the cervix (Patients with previous malignancies are eligible if disease-free for >2 years)
20. History of stroke, unstable angina, myocardial infarction, or ventricular arrhythmia requiring medication or a pacemaker within the last 6 months prior to Screening
21. Unstable or severe uncontrolled medical condition (e.g., unstable cardiac function, unstable pulmonary condition, uncontrolled diabetes) or any important medical illness or abnormal laboratory finding that would, in the Investigator's judgment, increase the risk to the patient associated with his or her participation in the study
22. Known hypersensitivity to duvelisib and/or its excipients

Dose Modifications

If a patient has an AE at least possibly related to duvelisib, then dose interruptions with possible modifications (e.g., reduction to 50 mg, 25 mg, or 15 mg BID) and toxicity management may be implemented as noted in Table 1.

TABLE 1 duvelisib dose modifications and toxicity management

| Treatment Related Toxicity[1,2] | Adverse Reaction Grade | Duvelisib Dose Modification and Toxicity Management |
|---|---|---|
| Nonhematologic Adverse Reactions | | |
| Infections | Grade 3 or higher infection | Withhold until resolved<br>Resume at the same or reduced dose |
| | Clinical CMV infection or viremia (positive PCT or antigen test) | Withhold until resolved<br>Resume at the same or reduced dose<br>If duvelisib is resumed, monitor patients for CMV reactivation (by PCR or antigen test) at least monthly |
| | PJP | For suspected PJP, withhold duvelisib until evaluated<br>For confirmed PJP, discontinue duvelisib |
| Non-infectious Diarrhea or colitis | Mild/moderate diarrhea (Grade 1-2, up to 6 stools per day over baseline) and responsive to antidiarrheal agents,<br>OR<br>Asymptomatic (Grade 1) colitis | No change in dose<br>Initiate supportive therapy with antidiarrheal agents as appropriate<br>Monitor at least weekly until resolved |
| | Mild/moderate diarrhea (Grade 1-2, up to 6 stools | Withhold until resolved<br>Initiate supportive therapy |

TABLE 1-continued

| duvelisib dose modifications and toxicity management | | |
|---|---|---|
| Treatment Related Toxicity[1,2] | Adverse Reaction Grade | Duvelisib Dose Modification and Toxicity Management |
| | per · day over baseline) and unresponsive to antidiarrheal agents | with enteric acting steroids (e.g., budesonide)<br>Monitor at least weekly until resolved<br>Resume at a reduced dose |
| | Abdominal pain, stool with mucus or blood, change in bowel habits, peritoneal signs,<br>OR<br>Severe diarrhea (Grade 3, >6 stools per day over baseline) | Withhold until resolved<br>Initiate supportive therapy with enteric acting steroids (e.g., budesonide) or systemic steroids<br>Monitor at least weekly until resolved<br>Resume at a reduced dose<br>For recurrent Grade 3 diarrhea or recurrent colitis of any grade, discontinue |
| Cutaneous reactions | Grade 1-2 | No change in dose<br>Initiate supportive care with emollients, anti-histamines (for pruritus), or topical steroids<br>Monitor closely |
| | Grade 3 | Withhold until resolved<br>Initiate supportive care with emollients, anti-histamines (for pruritus), or topical steroids<br>Monitor at least weekly until resolved<br>Resume at reduced dose<br>If severe cutaneous reaction does not improve, worsens, or recurs, discontinue |
| Pneumonitis without suspected infectious cause | Moderate (Grade 2) symptomatic pneumonitis | Withhold<br>Treat with systemic steroid therapy<br>If pneumonitis recovers to Grade 0 or 1, duvelisib may be resumed at reduced dose |
| ALT/AST elevation | 3 to 5 × upper limit of normal (ULN) (Grade 2) | Maintain duvelisib dose<br>Monitor at least weekly until return to <3 × ULN |
| | >5 to 20 × ULN (Grade 3) | Withhold duvelisib and monitor at least weekly until return to <3 × ULN<br>Resume duvelisib at same dose (first occurrence) or at a reduced dose for subsequent occurrence |
| Hematologic adverse reactions | | |
| Febrile neutropenia | Grade 3-4 | Withhold duvelisib until afebrile and resolution of Grade 3 or Grade 4 neutropenia to Grade ≤2 (ANC >1.0 Gi/L)<br>Monitor ANC at least weekly until >1.0 Gi/L<br>Resume at same dose (first occurrence) or at a reduced dose for subsequent occurrence |
| Neutropenia | Absolute neutrophil count (ANC) 0.5 to 1.0 Gi/L | Maintain duvelisib dose<br>Monitor ANC at least weekly |
| | ANC less than 0.5 Gi/L | Withhold duvelisib<br>Monitor ANC until >0.5 Gi/L<br>Resume at same dose (first occurrence) or at a reduced dose for subsequent occurrence |
| Thrombocytopenia | Platelet count 25 to <50 Gi/L (Grade 3) with Grade 1 | No change in dose<br>Monitor platelet counts at |

TABLE 1-continued

| duvelisib dose modifications and toxicity management | | |
|---|---|---|
| Treatment Related Toxicity[1,2] | Adverse Reaction Grade | Duvelisib Dose Modification and Toxicity Management |
| | bleeding | least weekly |
| | Platelet count 25 to <50 Gi/L (Grade 3) with Grade 2 bleeding or Platelet count <25 Gi/L (Grade 4) | Withhold duvelisib Monitor platelet counts until ≥25 Gi/L and resolution of bleeding (if applicable) Resume at same dose (first occurrence) or resume at a reduced dose for subsequent occurrence |

Abbreviations: ALT = alanine aminotransferase; ANC = absolute neutrophil count; AST = aspartate aminotransferase; CMV = cytomegalovirus; DRESS = drug reaction with eosinophilia and systemic systems; Gi = 1 × 109; PCR = polymerase chain reaction; PJP = Pneumocystis jirovecii; pneumonia; SJS = Stevens-Johnson syndrome; TEN = toxic epidermal necrolysis; ULN = upper limit of normal

[1]Treatment-related toxicity: possible, probable, or definite relationship to study treatment

[2]Toxicity grades are defined per CTCAE version 5.0. Note if parameter is not defined by CTCAE, then AE grading criteria should be utilized.

Duvelisib may be held up to 42 days for toxicity.

The severity of AE will be graded according to the NCI CTCAE, version 5.0 (see web page at http://ctep.cancer.gov for details). AEs not listed in the CTCAE should be graded as summarized in Table 2.

TABLE 2

| CTCAE grading | | |
|---|---|---|
| CTC grade | Equivalent to | References to |
| 1 | Mild | Discomfort noticed but no disruption of normal daily activity |
| 2 | Moderate | Discomfort sufficient to reduce or affect daily activity; no treatment or medical intervention is indicated although this could improve the overall well-being or symptoms of the patient |
| 3 | Severe | Inability to work or perform normal daily activity; treatment or medical intervention is indicated in order to improve the overall well-being or symptoms; delaying the onset of treatment is not putting the survival of the patient at direct risk |
| 4 | Life-threatening/disabling | An immediate threat to life or leading to a permanent mental or physical conditions that prevents work or performing normal daily activities; treatment or medical intervention is required in order to maintain survival |
| 5 | Death | AE resulting in death |

Example 2. A Phase 2, Randomized, Open-label, 2-Arm Study Comparing 2 Intermittent Dosing Schedules of Duvelisib in Subjects With Indolent Non Hodgkin Lymphoma (iNHL)

This study is a phase 2, randomized, open-label, 2 arm study designed to evaluate the efficacy and safety of prescribed drug holidays of duvelisib treatment in subjects with relapsed/refractory iNHL who have received at least 1 prior systemic therapy.

The primary objective of this experiment is to determine the effects of predefined 2 week duvelisib dose holidays on tumor responses and safety/tolerability.

In one arm, duvelisib will be administered as 25 mg BID continuously for 10 weeks, followed by 25 mg BID dosed two weeks on and two weeks off of each subsequent 4-week cycles. In a second arm, duvelisib will be administered as 25 mg BID dosed two weeks on and two weeks off.

The primary outcome measures of this experiment is objective response rate (ORR) [Time Frame: 36 months], which is proportion of subjects achieving a CR or PR will be estimated as per IWG Criteria.

Secondary outcome measures of this experiment includes PFS (Progression Free Survival) [Time Frame: 5 years] from time of first dose of study intervention to PD or death; ORR (Objective Response Rate) [Time Frame: ORR estimated at 6, 12, 18, and 24 months after first dose of study intervention.]; Proportion of subjects achieving a CR or PR will be estimated as per Lugano Criteria; DOR (Duration of Response) [Time Frame: 5 years] from the time of first response to PD using KM methods; OS (Overall Survival) [Time Frame: 5 years] from time of first dose of study intervention to death; LNRR (Lymph Node Response Rate) [Time Frame: 36 months] calculated as the proportion of subjects achieving≥50% decrease in the SPD of target lymph nodes; TTFR (Time To First Relapse) [Time Frame: 36 months] from the time of first dose of study intervention to time of first CR or PR; Number of participants with treatment-emergent adverse events as assessed by CTCAE v5.0 [Time Frame: 36 months] from the time of screening to the end of Safety Follow-Up period of the study; Peak Plasma Concentration (Cmax) [Time Frame: 36 months]; TTF (Time To Treatment Failure) [Time Frame: 5 years] from first dose of study intervention until discontinuation for any reason and will be summarized using KM methods; and area under the plasma concentration versus time curve (AUC) [Time Frame: 36 months]

Inclusion Criteria:

- Age≥18 years, ECOG performance status≤2
- Histologically confirmed diagnosis of iNHL (Subtypes include FL Grades 1 to 3a, marginal zone lymphoma (splenic, nodal, or extranodal), or SLL
- Must have received 1 prior systemic regimen for iNHL
- Must have documented radiologic evidence of disease progression, and at least 1 bi-dimensionally measurable lesion≥1.5 cm (which has not been previously irradiated), according to 2007 revised IWG criteria
- Must have adequate organ function defined by the following laboratory parameters:
  - Absolute neutrophil count (ANC)≥1.0×10^9/L
  - Platelet count≥75×10^9/L
  - Serum creatinine<2.0 mg/dL (197 μmon)

Total bilirubin≤1.5×upper limit of normal (ULN) (exception: subjects with Gilbert's Syndrome may have a bilirubin>1.5×ULN)

Aspartate transaminase (AST)/serum glutamic-oxaloacetic transaminase (SGOT) and alanine aminotransferase (ALT)/serum pyruvic transaminase (SGPT) ≤3.0×ULN Exclusion Criteria:

Anticancer treatment, major surgery, or use of any investigational drug within 28 days before the start of study intervention; palliative radiation therapy is allowed if>7 days and any toxicity is Grade≤1

Clinical or histological evidence of transformation to a more aggressive subtype of lymphoma or grade 3b FL or Richters' transformation or CLL Prior allogeneic hematopoietic stem cell transplant (HSCT); treatment with a PI3K inhibitor History of drug-induced colitis or pneumonitis; TB treatment≤2 years prior to randomization; administration of a live or live attenuated vaccine within 6 weeks of randomization Ongoing treatment with chronic immunosuppressants or systemic steroids or treatment for systemic bacterial, fungal, or viral infection Active cytomegalovirus (CMV) or Epstein-Barr virus (EBV) infection Unable to receive prophylactic treatment for pneumocystis, herpes simplex virus (HSV), or herpes zoster (VZV) at screening Concurrent administration of medications or foods that are strong inhibitors or inducers of cytochrome P450 3A (CYP3A). No prior use within 2 weeks before the start of study intervention.

Baseline QTcF>500 ms

Concurrent active malignancy other than non-melanoma skin cancer or carcinoma in situ of the cervix, bladder cancer, or prostate cancer not requiring treatment. Subjects with previous malignancies are eligible if they have been disease-free for 2 years or more.

Unstable or severe uncontrolled medical condition that would, in the Investigator's judgment, increase the subject's risk to participating in this study.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A method of treating peripheral T-cell lymphoma in a human subject in need thereof, the method comprising:

(i) orally administering to the subject 75 mg of duvelisib, or a pharmaceutically acceptable form thereof, twice daily for a first interval; and (ii) orally administering to the subject 25 mg of duvelisib, or a pharmaceutically acceptable form thereof, twice daily for a second interval;

thereby treating the subject.

2. The method of claim 1, wherein the first interval is at least 4 weeks.

3. The method of claim 1, wherein the first interval is 8 weeks.

4. The method of claim 1, wherein the second interval is at least 4 weeks.

5. The method of claim 1, wherein the peripheral T-cell lymphoma is relapsed or refractory.

6. A method of treating indolent non-Hodgkin lymphoma in a human subject in need thereof, the method comprising:

(i) orally administering to the subject 25 mg of duvelisib, or a pharmaceutically acceptable form thereof, twice daily for 12 weeks; and a cycle comprising:

(ii) abstaining from orally administering duvelisib, or a pharmaceutically acceptable form thereof, for 2 weeks; and (iii) orally administering to the subject 25 mg of duvelisib, or a pharmaceutically acceptable form thereof, twice daily for 2 weeks;

thereby treating the subject.

7. The method of claim 6, wherein the cycle is repeated at least once.

* * * * *